United States Patent [19]

Fritz et al.

[11] 3,951,939

[45] Apr. 20, 1976

[54] POLYPEPTIDES, PROCESS FOR THEIR MANUFACTURE AND THEIR USE AS POLYVALENT ISOINHIBITORS

[75] Inventors: Hans Fritz, Hohenbrunn; Laszlo Beréss; Rosemarie Beréss, both of Ottendorf; Brunhilde Fórg-Brey, Munich, all of Germany

[73] Assignee: Behringwerke Aktiengesellschaft, Marburg, Lahn, Germany

[22] Filed: July 8, 1974

[21] Appl. No.: 486,223

Related U.S. Application Data

[63] Continuation-in-part of Ser. No. 478,791, June 12, 1974, abandoned, which is a continuation of Ser. No. 321,301, Jan. 5, 1973, abandoned.

[30] Foreign Application Priority Data

July 7, 1973 Germany............................ 2334564

[52] U.S. Cl..................... 260/112 R; 260/112.5 R; 424/177
[51] Int. Cl.²................... C07C 103/52; C07G 7/00; C08H 1/00
[58] Field of Search...................... 260/112.5, 112 R

[56] References Cited

UNITED STATES PATENTS

| | | | |
|---|---|---|---|
| 2,890,986 | 6/1959 | Kraut et al........................ | 424/177 |
| 3,181,997 | 5/1965 | Schultz............................ | 260/112.5 |
| 3,300,384 | 1/1967 | Schultz............................ | 424/177 |
| 3,308,026 | 3/1967 | Schultz............................ | 424/177 |
| 3,558,773 | 1/1971 | Schultz............................ | 260/112.5 |

Primary Examiner—Lewis Gotts
Assistant Examiner—Reginald J. Suyat
Attorney, Agent, or Firm—Henry W. Koster

[57] ABSTRACT

The present invention relates to polypeptides, to a process for isolating them from sea-anemones (Actinaria), preferably from Anemonia Sulcata, and their use as polyvalent isoinhibitors for proteases, peptidases and esterases such as trypsin, chymotrypsin, plasmin and Kallicrein.

17 Claims, No Drawings

POLYPEPTIDES, PROCESS FOR THEIR MANUFACTURE AND THEIR USE AS POLYVALENT ISOINHIBITORS

The present application is a continuation-in-part application of U.S. Pat. application Ser. No. 478,791 filed June 12, 1974, which in turn was a continuation of application Ser. No. 321,301 filed Jan. 5, 1973, both said applications having been abandoned.

The present invention relates to polypeptides, to a process for isolating them from sea-anemones (Actinaria), preferably from Anemonia Sulcata, and their use as polyvalent isoinhibitors for proteases, peptidases and esterases such as trypsin, chymotrypsin, plasmin and Kallicrein.

Inhibitors are designated as being polyvalent if they inhibit several enzymes. Since they are a mixture of inhibitors which are differing, although to a minor degree only, in their build-up and composition of amino-acids, they are called "isoinhibitors". Thus, they are a mixture of proteins with equal function, but of different primary structure.

The activity of these inhibitors is measured with inhibitor units: the inhibiting unit (IU) is the inhibitor quantity which under standard conditions reduces the reaction rate of an enzyme by 1 $\mu$ mol/min.

Processes for the isolation of inhibitors from serum and from various animal and vegetable tissues such as organs (lungs, pancreas, parotids) of bovines, submandibular glands of canides and felides, beans, maize, potatoes, corn and peanuts have already been described.

The inhibitors obtained from the serum have a relatively high molecular weight. Since, with an increasing molecular weight, the antigenicity of polypeptides generally increases also, a high molecular weight is undesirable. Moreover, owing to a high molecular weight, the penetration power of the inhibitors is lower than that of low-molecular-weight inhibitors.

Being expensive, serum is not suitable as starting material for obtaining inhibitors.

Inhibitors isolated from vegetable material have hitherto not been used because owing to their high molecular weight they have immunogenic activity and cause side-reactions which are due to side products which are difficult to separate.

From inhibitors isolated from animal tissues it is known that they are stored selectively in the kidneys, owing to their high isoelectric point.

The present invention provides polypeptides with the following composition of amino-acids:

| Amino acid | Number of molecules |
|---|---|
| Aspartic acid | 5 – 7 |
| Threonine | 1 – 3 |
| Serine | 2 – 5 |
| Glutamic acid | 3 – 7 |
| Proline | 2 – 4 |
| Glycine | 6 – 7 |
| Alanine | 2 – 5 |
| Cysteine | 6 |
| Valine | 2 – 4 |
| Isoleucine | 1 – 2 |
| Leucine | 1 – 3 |
| Tyrosine | 3 – 4 |
| Phenyl-alanine | 2 – 4 |
| Histidine | 1 – 2 |
| Lysine | 2 – 4 |
| Arginine | 4 – 7 | and that their molecular weights are in the range of from 5200 to 7800, preferably from 5800 to 7100, and that their isoelectric points are between pH 4.5 and pH 9.5, preferably between pH 6.0 and 7.5.

The present invention furthermore relates to a process for isolating polypeptides, wherein sea-anemones, preferably Calliactis parasitica, Condylactis aurantiaca, Actinia aquina, Cribrinopsis crassa, Metridium senite and, in particular Anemonia sulcata, are extracted with an aqueous medium, and the polypeptides obtained from the extract are enriched and isolated therefrom, preferably by ion exchange or affinity chromatography methods.

The tentacles of the sea-anemones are especially rich in polypeptides according to the invention.

Before the extract is worked up by chromatography, contaminations may be precipitated by means of organic solvents miscible with water, for example ketones, such as acetone, alcohols such as ethanol, or ethers such as diethyl ether. If an alcohol is used for extraction purposes, it is a simple operation to precipitate the contaminants by increasing the corresponding alcohol concentration. According to a first purification step which is especially advantageous, the sea-anemone extract is heated for some minutes at temperatures of from 55° to 95°C, preferably of 65°C.

For the extraction operation, about 1 to 5 times the weight of extracting agent is used, calculated on the weight of the sea-anemones. Suitable extraction agents are, in addition to water, especially mixtures of water and organic solvents miscible with water, above all the above-cited ketones, alcohols and ethers. The ratio of water to solvent in such a mixture may vary greatly. It is essential, however, that the ratio be such as to provide a homogenous phase of the two components.

The preferred extraction agents are water-alcohol mixtures, the alcohol component being, in addition to the preferable ethanol, further alcohols miscible with water. Particularly good yields are obtained using a 96 % aqueous ethyl alcohol for the extraction and choosing a ratio of anemones to solvents of 1 : 1 (weight to volume). Instead of aqueous-alcoholic extraction agents, aqueous salt solutions or water may also be used for this purpose.

For enriching and isolating the polypeptides from the crude extract or from a pre-purified extract obtained according to one of the above-cited methods, the polypeptides of the invention are advantageously adsorbed in a low-conductivity medium on ion exchangers having acid functional groups at a weakly acid pH-value. After the non-adsorbed portion has been separated, the ion exchanger is treated with an aqueous solution of increased conductivity and at a weakly basic pH-value to isolate the polypeptides by elution. When using carboxymethyl-cellulose ion exchangers, adsorption of the polypeptides of the invention is brought about at a conductivity of 0 to 6 mS (milliSiemens) preferably at 2 – 4 mS, and at a pH-value of 4.5 to 6.8, preferably at a pH of 5. To obtain an optimum yield, it is recommended to test by known methods if, on the one hand, the adsorption conditions chosen permit a linkage of the polypeptides to the adsorbent and, on the other hand, the elution conditions afford the desired yeild of polypeptides. These measures taken into regard, any acid ion exchanger having, for example functional carboxymethyl, sulfoethyl, sulfopropyl or phosphate groups are, of course, suitable as adsorbent for the polypeptides of the invention, if the conditions are varied adequately. It is especially advantageous to carry out the adsorption and elution in a chromatography column and to allow for a gradient increase in conductivity and in the pH-value of the elution buffer solution. Where required or desired, the product resulting from the first purification by chromatography may further be purified, advantageously according to column chromatography using molecular sieves which exclude molecular weights of about 10,000. Cross-linked dextran (Sephadex$^{(R)}$ G-50, Pharmacia), Agarose (Biogel A$^{(R)}$ 5 M, Biorad Lab.) or a polyacrylamide resin (Biogel P$^{(R)}$ 10, Biorad Lab.) are preferred for this purpose.

The polypeptides of the invention may also be obtained in a single process step by means of water-insoluble commercial trypsin derivatives (for example, so-called trypsin resins). To this effect, the water-insoluble trypsin derivative is placed into a clarified homogeneous extract of sea-anemones, the polypeptide-trypsin derivative complex formed is separated and the polypeptides are desorbed at an acid pH from the trypsin derivative by means of an alkali metal chloride solution in hydrochloric acid. After neutralization, the polypeptide solution is concentrated, for example in a vacuum rotatory evaporator, demineralized and lyophilized.

The polypeptides of the invention are polyvalent isoinhibitors which, when prepared according to the process of this invention, have a specific activity of 1.5 to 3.3 IU/mg of protein.

Depending on the species or mixtures of various species of anemones used, polypeptide mixtures obtained from the anemones may be separated, for example by ion exchange chromatography, into more or less numerous polypeptides.

Water-insoluble trypsin derivatives may also be used for a high-degree purification of polypeptides obtained from sea-anemones. For this purpose, the polypeptides which have been pre-purified by chromatography are adsorbed on the trypsin derivative and then again desorbed by the known method of affinity chromatography. The polypeptide-trypsin complex is preferably dissociated in the acid range, for example at a pH-value of from 1 to 3, advantageously from 1.5 to 2.5.

The trypsin derivatives are used in an amount of from 1 to 20 grams, preferably 5 to 10 grams, calculated on 1 kg of sea-anemones.

The polypeptides of the invention may be concentrated and made storable by known methods, for example by ultra-filtration and/or lyophilization. The increase in concentration can be checked by determining the inhibiting activity of the polypeptides but also by establishing the UV absorption at 280 nm.

The polypeptides of the invention are free from the known toxins of the sea-anemones. This is established by intramuscular injection of 1 mg of polypeptide to the shore-crab Carcinus maenas. This crab does not show vibration of muscles, ataxia of extremities nor spasms, if a preparation is free from toxins.

For determining the enzymatic activity (cf. H.U. BERGMEYER "Methoden der enzymatischen Analyse", second edition, vol. 1, 1970, page 1011 et seq.), use is made of the optical absorption of a compound split off by the enzyme. Thus, N-benzoyl-DL-arginine-p-nitroanilide is used for the trypsin and plasmin and N-3-(carboxypropionyl)-L-phenylalanine-p-nitroanilide for chymotrypsin as a substrate, and the optical absorption of the split-off p-nitroaniline is then measured.

As a measure of the kallikrein activity, the splitting of the benzoyl-L-arginine ethyl ether is used. The ethanol set free thereby is oxidized in the presence of nicotine amide-adenine-dinucleotide by means of alcohol-dehydrogenase. The extinction of the reduced nicotine amide-adenine dinucleotide is then measured.

If these reactions are carried out in the presence of inhibitors, the splitting reactions are inhibited. As a consequence the optical absorption is lower and is then a measure of the inhibiting activity of the inhibitor.

For the analysis of the composition of amino acids, 300 μg of the polypeptides are hydrolyzed in 6N hydrochloric acid at 110°C and evaluated in an amino acid analyzer.

The molecular weights are determined by means of gel filtration using reference substances or calculated from the composition of the amino acids. The tolerance limits of these measurements are about ± 10 %.

The isoelectric points are determined by electrophoresis.

The polypeptides of the invention inactivate proteinases and esterases. Their particular importance is in the field of the inactivation of proteinases and esterases of plasma and of blood cells. They also have an influence on the catalytic interaction of individual factors of the coagulation and fibrinolysis. They may be used in the therapy of bleedings caused by excessive fibrinolysis (hyperplasminemia), after the treatment for consumption coagulopathy and for substituting consumed coagulation factors (fibrinogen, factor V, factor VIII).

The following Examples illustrate the invention:

Isolation of the crude toxin 1 kg of sea anemones Anemonia sulcata (specific inhibitor activity about 1.0 IU/g) were extracted three times with 100 ml portions of 50 % aqueous ethanol. The extracts were combined, concentrated under reduced pressure to a volume of 50 ml and mixed with 50 ml of ethanol, 300 ml of acetone and 100 ml of ether. A brown precipitate was formed which was isolated by centrifugation, dissolved in 50 ml of distilled water and lyophilized. From 1 kg of starting material, 3 g of crude toxin having a specific inhibitor activity of 0.39 IU/mg were obtained.

EXAMPLE 1

Isolation of the crude polypeptides

A.

20 g of crude toxin were dissolved in 200 ml of 0.1-molar sodium acetate buffer having a pH-value of 5.5 and poured on a carboxymethyl-Sephadex C-50 column (7 × cm) equilibrated to pH of 5.5 with 0.1 molar sodium acetate buffer. The toxins were then eluted with 7 liters of 0.1-molar acetate buffer, then with 4 liters of 0.2 molar acetate buffer and eventually with 6 liters of 0.4-molar acetate buffer; thereby also impurities were eluted. The mixture of the polypeptides was then isolated with 8 liters of 0.2-molar acetate buffer, which also contained 5 % of sodium chloride. The fractions which had the highest inhibitor activity were combined (300 ml) and dialyzed for 16 hours against distilled water and then lyophilised. 2 g of crude polypeptide were obtained from 20 g of crude toxin.

B.

20 g of crude toxin were worked up as described under A and the combined fractions with the highest inhibitor activity (300 ml) were saturated with 200 g of solid ammonium sulfate. The polypeptide-containing precipitate thereby formed was isolated by centrifugation. The salts that had remained in the precipitate were separated by fractionation on a Sephadex G-15 column.

Purification of the crude polypeptides 2 g of crude polypeptide prepared as described under A. were dissolved in a 0.1-molar Tris/hydrochloric acid buffer having a pH-value of 8.0 and which contained 1 mole of sodium hydrochloride, and purified on a Sephadex G-50 column (5.5 × 110 cm), which had been equilibrated with a solution of a 0.1 molar Tris/hydroxymethyl-aminomethane/hydrochloric acid buffer to a pH-value of 8.0 and 1 mole of sodium chloride. The fraction eluted last (300 ml) was concentrated in a vacuum rotary evaporator to a volume of 80 ml and combined with 31 g of solid ammonium sulfate. A precipitate of 400 mg of polypeptide mixture was formed which was made salt-free on a Sephadex G-15 column. The eluate was freeze-dried, whereby glossy colorless leaflets having a specific activity of 3.3 IU/mg were obtained.

Separation into the individual polypeptides.

5 ml of polypeptide solution, 50 mg of polypeptide mixture having a specific inhibitor activity of 3.3 IU/mg, dissolved in 0.05-molar triethanolamine/hydrochloric acid solution having a pH-value of 8.5, were separated by passage on a carboxymethyl cellulose column (1.3 × 18 cm) (the carboxymethyl cellulose was previously equilibrated with triethanolamine/hydrochloric acid solution having a pH-value of 8.5). Passage was carried on to fraction 106 (one fraction corresponds to 5.4 ml) with an elution speed of 11 ml/hour with a 0.05-molar triethanolamine/hydrochloric acid solution of pH 8.5, from fraction 107 on to fraction 300 with a linear gradient of 500 ml of 0.05-molar triethanolamine/hydrochloric acid solution of pH 8.5 which contained 0.1 mole of sodium chloride and 500 ml of 0.05 molar triethanolamine/hydrochloric acid solution having a pH-value of 8.5.

From the 300 original fractions, there were obtained by corresponding combination 7 fractions having increasing basicity and the following inhibiting activities:

| Fraction | A | 4.2 % | $C_3$ | 6.6 % |
|---|---|---|---|---|
| | B | 17.5 % | $C_4$ | 22.0 % |
| | $C_1$ | 10.5 % | D | 5.4 % |
| | $C_2$ | 22.5 % | | 88.7 % |

The individual polypeptide fractions having inhibiting activity were adjusted to pH 5 by means of a small amount of glacial acetic acid, concentrated in a vacuum rotary evaporator to 1/10 of their initial volume, rendered salt-free by passage through a column containing a molecular sieve material on the basis of polyacrylamide, "Bio-Gel P-2" (51.5 cm × 2 cm) and freeze-dried.

Rechromatography of fractions $C_2$ and $C_4$

The two fractions $C_2$ and $C_4$ were dissolved in 10 ml portions of the equilibration buffer described in the preceding paragraph, introduced into the CM-cellulose column and developed with the linear gradient into the individual polypeptides as described for the separation.

From both fractions, the respective sub-fractions $C_{2a}$ and $C_{2b}$ as well as $C_{4a}$ and $C_{4b}$ were isolated. Concentration a and desalting were carried out as described above. Also these fractions were freeze-dried.

Isolation with the aid of water-insoluble trypsin resins 1 kg of Sea anemones was homogenized in 3 liters of distilled water and centrifuged. The supernatant was decanted off and combined with 300 ml of 0.4 molar sodium chloride and 0.1 molar triethanol-amine hydrochloride having a pH-value of 8.0. 5 g of water-insoluble trypsin resin which had been washed with a solution of 0.1-molar triethanolamine of pH 8 and 0.4 mole of sodium chloride, were suspended for 1 hour at 4°C in this extraction solution and the whole was then centrifuged. The precipitate of polypeptide and trypsin resin was washed thrice in the afore-mentioned triethanolamine/sodium chloride buffer solution and centrifuged, with 3000 rev./min. for 2 minutes. Thereby, only the resin sedimented, but not the fine floating particles dragged in. The sediment was suspended several times in 100 of ice-cooled 0.4-molar potassium chloride/hydrochloric acid solution of pH 2.0 and centrifuged. The supernatants were combined and contained 90 % of the polypeptide bound by the trypsin resin. The polypeptide solutions were neutralized with 0.1-N sodium hydroxide solution, concentrated in a vacuum rotary evaporator at a bath temperature of 20°C, rendered salt-free by passage through a Bio-Gel P-2 column and freeze-dried. The specific inhibitor activity of the freeze-dried polypeptide was found to be 2.4 IU/mg, which corresponded to an enrichment by the factor 2000, referred to the inhibitor content of sea-water wet sea anemones.

Further purification was carried out on a Sephadex G-50 column which had been equilibrated with a solution of 0.1-molar Tris/hydroxymethyl-aminomethane/-hydrochloric acid buffer of pH 8.0 and 1-molar sodium chloride. Freeze-drying of the desalted eluate yielded glossy colorless leaflets having a specific inhibitor activity of 3.3 IU/mg.

The following Table indicates the compositions of the amino acids of the product according to the invention, of the sub-fractions isolated therefrom A, B, $C_{2a}$ and $C_{4b}$ as well as of two polypeptide inhibitors prepared according to the prior art from cattle's organs and cattle' colostrum, and moreover the molecular weights.

TABLE

| Amino acid | claimed product polypeptide mixture | fractions | | | | | cattle's organs | cattle's colostrum |
|---|---|---|---|---|---|---|---|---|
| | | A | B | $C_{2a}$ | $C_{4b}$ | D | | |
| Aspartic acid | 6 | 6 | 6 | 6 | 6 | 6 | 5 | 8 |
| Threonine | 1 | 1 | 1 | 1 | 1 | 1 | 3 | 6 |
| Serine | 3 – 5 | 5 | 4 | 3 | 4 | 1 | 3 | |
| glutamic acid | 4 – 5 | 5 | 5 | 5 | 5 | 4 | 4 | 10 |
| Proline | 2 – 3 | 3 | 3 | 3 | 2 | 2 | 4 | 7 |
| Glycine | 6 – 7 | 6 | 6 | 7 | 7 | 6 | 6 | 4 |
| Alanine | 2 | 2 | 2 | 2 | 2 | 2 | 6 | 4 |
| Cysteine | 6 | 6 | 6 | 6 | 6 | 6 | 6 | 6 |
| Valine | 4 | 4 | 4 | 4 | 4 | 4 | 1 | — |

TABLE-continued

| Amino acid | claimed product polypeptide mixture | A | B | fractions C$_{2a}$ | C$_{4b}$ | D | cattle's organs | cattle's colostrum |
|---|---|---|---|---|---|---|---|---|
| Met | 0 | 0 | 0 | 0 | 0 | 0 | 1 | 1 |
| Isoleucine | 1 – 2 | 2 | 2 | 2 | 2 | 1 | 2 | 1 |
| Leucine | 2 – 3 | 2 | 2 | 2 | 3 | 2 | 2 | 5 |
| Tyrosine | 3 | 3 | 3 | 3 | 3 | 3 | 4 | 3 |
| Phenylalanine | 2 – 3 | 2 | 2 | 3 | 3 | 3 | 4 | 4 |
| Lysine | 3 – 4 | 4 | 4 | 4 | 3 | 3 | 4 | 2 |
| Histidine | 1 – 2 | 2 | 2 | 1 | 1 | 1 | — | — |
| Arginine | 5 – 7 | 5 | 5 | 6 | 7 | 6 | 6 | 3 |
| Tryptophane | 0 | 0 | 0 | 0 | 0 | 0 | 0 | 0 |
| Sum | | 58 | 58 | 59 | 58 | 54 | 58 | 67 |
| Molecular weight | | 6484 | 6484 | 6620 | 6577 | 6095 | 6513 | 7520 |

Tryptophane is not contained in the polypeptide inhibitor obtained from cattle's organs nor in the product of the invention and its sub-fractions. Contrary to the inhibitor obtained from cattle's organs, the polypeptides of the invention and their sub-fractions do not contain methionine but they contain histidine. The analytical data of the amino acids of A and B are identical. It is possible that there is a difference in the amidation degree of these two fractions or that one of the sub-fractions has a split peptide linkage inside the polypeptide chain.

EXAMPLE 2

2 Kilograms of deep-frozen sea-anemones were mixed with 2 l of 96 % alcohol and homogenized for 2 minutes in a highspeed mixing device. The dirty brown homogenous substance was heated while stirring for 5 minutes in a water bath to 65°C and, after cooling to 25°C, it was centrifuged at 8000 r.p.m. The clear reddish brown supernatent substance containing the polypeptides was decanted. The green-colored centrifuged material was homogenized wiht 1 l of 60 % ethanol for 2 minutes and the residue was separated by centrifuging and eliminated. The supernatant solution was dialyzed against demineralized water up to a conductivity of 4 mS. Subsequently, acetic acid was added to the dialysate until a pH-value of 5 was reached, and 60 g of dry carboxymethyl cellulose were added while stirring. The pH-value was readjusted to 5. After a period of 4 hours, the adsorbent was separated by filtration, washed with a sodium acetate buffer solution of a conductivity of 4 mS and a pH of 5 and then eluted with 0.05-molar trishydroxy methylaminomethane buffer of pH 8, containing 1 mol of sodium chloride. 67.5 % of polypeptides having an inhibiting acitivty were found in the elute. The concentration was 60.5 times that of the starting material.

The carboxymethyl cellulose elute was concentrated to 30 times its initial concentration by ultra-filtration and the concentrate was subjected to a gel filtration on Sephadex$^{(R)}$ G-50, using a column of 7 × 120 cm. Development was effected with 2 % acetic acid (volume to volume). Those fractions having, in addition to their absorption at 280 nm, a proteinase-inhibiting activity according to the above-cited testing methods were collected. The yield was 66 % of inhibiting activity calculated on the starting material. The specific purity which could be measured as inhibitor effect, calculated on the absorption of the material at 280 nm, was about 3 to 7 IU/A$_{280}$ compared to 0.065 IU/A 280, depending on the fraction. Without further losses, the fractions having an inhibiting activity could be demineralized on Sephadex$^{(R)}$G-25 subsequently to this purification operation and then lyophilized.

Further purification could be carried out, where required by rechromatography of inhibitory polypeptides thus obtained on the cited ion exchangers. An increase in specific activity can, however, also be obtained by means of affinity chromatography on trypsin resins.

EXAMPLE 3

1 Kilogram of sea-anemones was thawed and the ectoderm and endoderm removed from the body. The two blastodermic layers were homogenized in 3 l of water and then centrifuged. The clear supernatant solution was combined with a 0.1-molar triethanolamine-HCl buffer of pH 8.0 containing 0.4 M of NaCl to adjust the pH to 8.0. 5 g of carboxymethyl cellulose trypsin were added to this extract which had been cooled to about 0°C. After 1 hour, a centrifuged sample did not show any inhibiting activity. The trypsin resin was separated from the supernatant solution and washed several times with the triethanolamine-HCl buffer of pH 8 and 0.4 M of NaCl until the filtrate was free from proteins. The trypsin resin containing the inhibitory polypeptides in adsorbed state was then treated with 0.4-molar KCl-HCl of pH 2.0, whereupon the inhibitory polypeptides were recovered in a yield of 95 %. The solution was neutralized by means of triethanolamine, concentrated to 1/30 of its volume and demineralized in a column having Biogel$^{(R)}$P 2. A lyophilized end product from this fractionation has a specific activity of 2.5 IU/mg of protein. The product obtained according to the above-cited method was a mixture of polypeptides having an inhibiting activity. It could be further separated, for example, as follows: 80 mg of the dry peptide mixture were dissolved in 3 ml of 0.1-molar triethanolamine-HCl buffer of pH 4.2. The solution was applied onto a chromatography column containing sulfopropylSephadex$^{(R)}$C-25 and being equilibrated with 0.1-molar triethanol-amine-HCl buffer of pH 6.8. Elution was performed using the buffer solution used for the equilibration, until the second absorption peak at 280 nm appeared. Subsequently, a pH gradient was made from the equilibrium buffer and from a 0.1-molar triethanolamine-HCl buffer solution of pH 8.5. After the pH of the eluate had reached 8.5, the column was developed by means of a salt gradient consisting of triethanolamine-HCl of pH 8.5 and the same buffer solution with an addition of 0.2-molar NaCl. A total of 10 marked absorption peaks at 280 nm having inhibiting activity were obtained. The yield was 98 %, calculated on the polypeptide mixture used. The individual polypeptides having a high salt content were demineralized by means of an ultra-filter, and concentrated until the desired concentration was reached.

Where required, the polypeptide solution could be dried by means of a rotatory evaporator and lyophilized.

The fractions obtained showed the compositions of amino acids and molecular weight as seen in the following Table:

|  | Amino acid | Number of molecules | molecular weight |
|---|---|---|---|
| Fraction I | Aspartic acid | 7 | 7.100 ± 10 % |
|  | Threonine | 3 |  |
|  | Serine | 2 |  |
|  | Glutamic acid | 7 |  |
|  | Proline | 4 |  |
|  | Glycine | 7 |  |
|  | Alanine | 5 |  |
|  | Cysteine | 6 |  |
|  | Valine | 2 |  |
|  | Isoleucine | 1 |  |
|  | Leucine | 3 |  |
|  | Tyrosine | 4 |  |
|  | Phenyl-alanine | 4 |  |
|  | Histidine | 1 |  |
|  | Lysine | 4 |  |
|  | Arginine | 4 |  |
| Fraction II | Aspartic acid | 7 | 6.900 ± 10 % |
|  | Threonine | 3 |  |
|  | Serine | 2 |  |
|  | Glutamic acid | 7 |  |
|  | Proline | 3 |  |
|  | Glycine | 7 |  |
|  | Alanine | 4 |  |
|  | Cysteine | 6 |  |
|  | Valine | 3 |  |
|  | Isoleucine | 1 |  |
|  | Leucine | 1 |  |
|  | Tyrosine | 4 |  |
|  | Phenyl-alanine | 4 |  |
|  | Histidine | 2 |  |
|  | Lysine | 2 |  |
|  | Arginine | 5 |  |
| Fraction III | Aspartic acid | 7 | 6.800 ± 10 % |
|  | Threonine | 3 |  |
|  | Serine | 2 |  |
|  | Glutamic acid | 6 |  |
|  | Proline | 3 |  |
|  | Glycine | 7 |  |
|  | Alanine | 4 |  |
|  | Cysteine | 6 |  |
|  | Valine | 3 |  |
|  | Isoleucine | 1 |  |
|  | Leucine | 1 |  |
|  | Tyrosine | 5 |  |
|  | Phenyl-alanine | 4 |  |
|  | Histidine | 1 |  |
|  | Lysine | 2 |  |
|  | Arginine | 5 |  |
| Fraction IV | Aspartic acid | 7 | 6.400 ± 10 % |
|  | Threonine | 3 |  |
|  | Serine | 2 |  |
|  | Glutamic acid | 6 |  |
|  | Proline | 2 |  |
|  | Glycine | 7 |  |
|  | Alanine | 4 |  |
|  | Cysteine | 6 |  |
|  | Valine | 3 |  |
|  | Isoleucine | 1 |  |
|  | Leucine | 1 |  |
|  | Tyrosine | 4 |  |
|  | Phenyl-alanine | 4 |  |
|  | Histidine | 2 |  |
|  | Lysine | 2 |  |
|  | Arginine | 4 |  |
| Fraction V | Aspartic acid | 7 | 6.700 ± 10 % |
|  | Threonine | 3 |  |
|  | Serine | 2 |  |
|  | Glutamic acid | 6 |  |
|  | Proline | 3 |  |
|  | Glycine | 7 |  |
|  | Alanine | 4 |  |
|  | Cysteine | 6 |  |
|  | Valine | 3 |  |
|  | Isoleucine | 1 |  |
|  | Leucine | 1 |  |
|  | Tyrosine | 4 |  |
|  | Phenyl-alanine | 4 |  |
|  | Histidine | 2 |  |

-continued

|  | Amino acid | Number of molecules | molecular weight |
|---|---|---|---|
|  | Lysine | 2 |  |
|  | Arginine | 5 |  |
| Fraction VI | Aspartic acid | 7 | 6.500 ± 10 % |
|  | Threonine | 3 |  |
|  | Serine | 2 |  |
|  | Glutamic acid | 5 |  |
|  | Proline | 3 |  |
|  | Glycine | 7 |  |
|  | Alanine | 4 |  |
|  | Cysteine | 6 |  |
|  | Valine | 3 |  |
|  | Isoleucine | 1 |  |
|  | Leucine | 1 |  |
|  | Tyrosine | 4 |  |
|  | Phenyl-alanine | 4 |  |
|  | Histidine | 1 |  |
|  | Lysine | 2 |  |
|  | Arginine | 5 |  |
| Fraction VII | Aspartic acid | 7 | 6.600 ± 10 % |
|  | Threonine | 3 |  |
|  | Serine | 2 |  |
|  | Glutamic acid | 6 |  |
|  | Proline | 3 |  |
|  | Glycine | 7 |  |
|  | Alanine | 3 |  |
|  | Cysteine | 6 |  |
|  | Valine | 3 |  |
|  | Isoleucine | 1 |  |
|  | Leucine | 2 |  |
|  | Tyrosine | 4 |  |
|  | Phenyl-alanine | 4 |  |
|  | Histidine | 1 |  |
|  | Lysine | 2 |  |
|  | Arginine | 5 |  |
| Fraction VIII | Aspartic acid | 5 | 5.900 ± 10 % |
|  | Threonine | 3 |  |
|  | Serine | 2 |  |
|  | Glutamic acid | 4 |  |
|  | Proline | 2 |  |
|  | Glycine | 6 |  |
|  | Alanine | 3 |  |
|  | Cysteine | 6 |  |
|  | Valine | 3 |  |
|  | Isoleucine | 1 |  |
|  | Leucine | 1 |  |
|  | Tyrosine | 4 |  |
|  | Phenyl-alanine | 4 |  |
|  | Histidine | 1 |  |
|  | Lysine | 2 |  |
|  | Arginine | 5 |  |
| Fraction IX | Aspartic acid | 7 | 6.500 ± 10 % |
|  | Threonine | 3 |  |
|  | Serine | 2 |  |
|  | Glutamic acid | 4 |  |
|  | Proline | 2 |  |
|  | Glycine | 6 |  |
|  | Alanine | 3 |  |
|  | Cysteine | 6 |  |
|  | Valine | 2 |  |
|  | Isoleucine | 2 |  |
|  | Leucine | 3 |  |
|  | Tyrosine | 4 |  |
|  | Phenyl-alanine | 4 |  |
|  | Histidine | 1 |  |
|  | Lysine | 2 |  |
|  | Arginine | 6 |  |
| Fraction X | Aspartic acid | 5 | 6.000 ± 10 % |
|  | Threonine | 3 |  |
|  | Serine | 2 |  |
|  | Glutamic acid | 3 |  |
|  | Proline | 2 |  |
|  | Glycine | 6 |  |
|  | Alanine | 3 |  |
|  | Cysteine | 6 |  |
|  | Valine | 2 |  |
|  | Isoleucine | 2 |  |
|  | Leucine | 3 |  |
|  | Tyrosine | 4 |  |
|  | Phenyl-alanine | 4 |  |
|  | Histidine | — |  |
|  | Lysine | 2 |  |
|  | Arginine | 6 |  |

When the polypeptide fractions I to X are used in different concentrations in test systems for determining trypsin, chymotrypsin, plasmin and kallikrein, the proteinase activities were inhibited to different extents. The following Table indicates the inhibitor amounts used in micrograms which lead to a 50 % inhibition of the presented enzymatic activities:

TABLE

| Fraction | I | II | III | IV | V | VI | VII | VIII | IX | X |
|---|---|---|---|---|---|---|---|---|---|---|
| Trypsin | 1.65 | 1.45 | 1.35 | 1.25 | 1.7 | 1.3 | 2.05 | 2.0 | 2.55 | 3.0 |
| Chymotrypsin | 8 | 7.5 | 7.0 | 6.5 | 7.0 | 7.0 | 12.5 | 8.5 | 15 | 9.5 |
| Plasmin | 13 | 7.5 | 7.5 | 6 | 7.5 | 6 | 12.5 | 9.5 | 16 | 20 |
| Kallikrein | 1.4 | 1.15 | 1.6 | 1.15 | 1.4 | 1.15 | 1.5 | 0.95 | 0.15 | 0.03 |

Optimum inhibiting values were obtained for
Trypsin using fraction V
chymotrypsin using fraction V
Plasmin using fractions V and VII and
kallikrein using fraction X.

We claim:
1. Polypeptides found in sea-anemones (Actinaria), which have the following composition of amino acids:

| Amino acids | Number of molecules |
|---|---|
| Aspartic acid | 5 – 7 |
| Threonine | 1 – 3 |
| Serine | 2 – 5 |
| Glutamic acid | 3 – 7 |
| Proline | 2 – 4 |
| Glycine | 6 – 7 |
| Alanine | 2 – 5 |
| Cysteine | 6 |
| Valine | 2 – 4 |
| Isoleucine | 1 – 2 |
| Leucine | 1 – 3 |
| Tyrosine | 3 – 4 |
| Phenylalanine | 2 – 4 |
| Histidine | 1 – 2 |
| Lysine | 2 – 4 |
| Arginine | 4 – 7 | and which have molecular weights in the range of from 5200 to 7800, preferably between 5800 and 7100, and isoelectric points between pH 4.5 and pH 9.5., preferably between pH 6.0 and pH 7.5.

2. A polypeptide as claimed in claim 1, having the following composition of amino-acids:

| Amino acids | Number of molecules |
|---|---|
| Aspartic acid | 7 |
| Threonine | 3 |
| Serine | 2 |
| Glutamic acid | 7 |
| Proline | 4 |
| Glycine | 7 |
| Alanine | 5 |
| Cysteine | 6 |
| Valine | 2 |
| Isoleucine | 1 |
| Leucine | 3 |
| Tyrosine | 4 |
| Phenylalanine | 4 |
| Histidine | 1 |
| Lysine | 4 |
| Arginine | 4 | and a molecular weight of 7100 ± 10 %.

3. A polypeptide as claimed as claimed in claim 1, having the following composition of amino acids:

| Amino acids | Number of molecules |
|---|---|
| Aspartic acid | 7 |
| Threonine | 3 |
| Serine | 2 |
| Glutamic acid | 4 |
| Proline | 3 |
| Glycine | 7 |
| Alanine | 4 |
| Cysteine | 6 |
| Valine | 3 |
| Isoleucine | 1 |
| Leucine | 1 |
| Tyrosine | 4 |
| Phenylalanine | 4 |
| Histidine | 2 |
| Lysine | 2 |
| Arginine | 5 | and a molecular weight of 6900 ± 10 %.

4. A polypeptide as claimed in claim 1, having the following composition of amino-acids:

| Amino acids | Number of molecules |
|---|---|
| Aspartic acid | 7 |
| Threonine | 3 |
| Serine | 2 |
| Glutamic acid | 6 |
| Proline | 3 |
| Glycine | 7 |
| Alanine | 4 |
| Cysteine | 6 |
| Valine | 3 |
| Isoleucine | 1 |
| Leucine | 1 |
| Tyrosine | 5 |
| Phenylalanine | 4 |
| Histidine | 1 |
| Lysine | 2 |
| Arginine | 5 | and a molecular weight of 6800 ± 10,%.

5. A polypeptide as claimed in claim 1, having the following composition of amino-acids:

| Amino acids | Number of molecules |
|---|---|
| Aspartic acid | 7 |
| Threonine | 3 |
| Serine | 2 |
| Glutamic acid | 6 |
| Proline | 2 |
| Glycine | 7 |
| Alanine | 4 |
| Cysteine | 6 |
| Valine | 3 |
| Isoleucine | 1 |
| Leucine | 1 |
| Tyrosine | 4 |
| Phenylalanine | 4 |
| Histidine | 2 |
| Lysine | 2 |
| Arginine | 4 | and a molecular weight of 6400 ± 10 %.

6. A polypeptide as claimed in claim 1, having the following composition of amino-acids:

| Amino acids | Number of molecules |
|---|---|
| Aspartic acid | 7 |

-continued

| Amino acids | Number of molecules |
|---|---|
| Threonine | 3 |
| Serine | 2 |
| Glutamic acid | 6 |
| Proline | 3 |
| Glycine | 7 |
| Alanine | 4 |
| Cysteine | 6 |
| Valine | 3 |
| Isoleucine | 1 |
| Leucine | 1 |
| Tyrosine | 4 |
| Phenylalanine | 4 |
| Histidine | 2 |
| Lysine | 2 |
| Arginine | 5 | and a molecular weight of 6700 ± 10 %.

7. A polypeptide as claimed in claim 1, having the following composition of amino-acids:

| Amino acids | Number of molecules |
|---|---|
| Aspartic acid | 7 |
| Threonine | 3 |
| Serine | 2 |
| Glutamic acid | 5 |
| Proline | 3 |
| Glycine | 7 |
| Alanine | 4 |
| Cysteine | 6 |
| Valine | 3 |
| Isoleucine | 1 |
| Leucine | 1 |
| Tyrosine | 4 |
| Phenylalanine | 4 |
| Histidine | 1 |
| Lysine | 2 |
| Arginine | 5 | and a molecular weight of 6500 ± 10 %.

8. A polypeptide as claimed in claim 1, having the following composition of amino-acids:

| Amino acids | Number of molecules |
|---|---|
| Aspartic acid | 7 |
| Threonine | 3 |
| Serine | 2 |
| Glutamic acid | 6 |
| Proline | 3 |
| Glycine | 7 |
| Alanine | 3 |
| Cysteine | 6 |
| Valine | 3 |
| Isoleucine | 1 |
| Leucine | 2 |
| Tyrosine | 4 |
| Phenylalanine | 4 |
| Histidine | 1 |
| Lysine | 2 |
| Arginine | 5 | and a molecular weight of 6600 ± 10 %.

9. A polypeptide as claimed in claim 1, having the following composition of amino-acids:

| Amino acids | Number of molecules |
|---|---|
| Aspartic acid | 5 |
| Threonine | 3 |
| Serine | 2 |
| Glutamic acid | 4 |
| Proline | 2 |
| Glycine | 6 |
| Alanine | 3 |
| Cysteine | 6 |
| Valine | 3 |
| Isoleucine | 1 |
| Leucine | 1 |
| Tyrosine | 4 |
| Phenylalanine | 4 |
| Histidine | 1 |
| Lysine | 2 |
| Arginine | 5 | and a molecular weight of 5900 ± 10 %.

10. A polypeptide as claimed in claim 1, having the following composition of amino-acids:

| Amino acids | Number of molecules |
|---|---|
| Aspartic acid | 7 |
| Threonine | 3 |
| Serine | 2 |
| Glutamic acid | 4 |
| Proline | 2 |
| Glycine | 6 |
| Alanine | 3 |
| Cysteine | 6 |
| Valine | 2 |
| Isoleucine | 2 |
| Leucine | 3 |
| Tyrosine | 4 |
| Phenylalanine | 4 |
| Histidine | 1 |
| Lysine | 2 |
| Arginine | 6 | and a molecular weight of 6500 ± 10 %.

11. A polypeptide as claimed in claim 1, having the following composition of amino-acids:

| Amino acids | Number of molecules |
|---|---|
| Aspartic acid | 5 |
| Threonine | 3 |
| Serine | 2 |
| Glutamic acid | 3 |
| Proline | 2 |
| Glycine | 6 |
| Alanine | 3 |
| Cysteine | 6 |
| Valine | 2 |
| Isoleucine | 2 |
| Leucine | 3 |
| Tyrosine | 4 |
| Phenylalanine | 4 |
| Histidine | — |
| Lysine | 2 |
| Arginine | 6 | and a molecular weight of 6000 ± 10 %.

12. A polypeptide as claimed in claim 1, having the following composition of amino-acids:

| Amino acids | Number of molecules |
|---|---|
| Aspartic acid | 6 |
| Threonine | 1 |
| Serine | 5 |
| Glutamic acid | 5 |
| Proline | 3 |
| Glycine | 6 |
| Alanine | 2 |
| Cysteine | 6 |
| Valine | 4 |
| Isoleucine | 2 |
| Leucine | 2 |
| Tyrosine | 3 |
| Phenylalanine | 2 |
| Histidine | 4 |
| Lysine | 2 |
| Arginine | 5 | and a molecular weight of 6500 ± 10 %

13. A polypeptide as claimed in claim 1, having the following composition of amino-acids:

| Amino acids | Number of molecules |
| --- | --- |
| Aspartic acid | 6 |
| Threonine | 1 |
| Serine | 4 |
| Glutamic acid | 5 |
| Proline | 3 |
| Glycine | 7 |
| Alanine | 2 |
| Cysteine | 6 |
| Valine | 4 |
| Isoleucine | 2 |
| Leucine | 2 |
| Tyrosine | 3 |
| Phenylalanine | 3 |
| Histidine | 4 |
| Lysine | 1 |
| Arginine | 6 | and a molecular weight of 6600 ± 10 %.

14. A polypeptide as claimed in claim 1, having the following composition of amino-acids:

| Amino acids | Number of molecules |
| --- | --- |
| Aspartic acid | 6 |
| Threonine | 1 |
| Serine | 3 |
| Glutamic acid | 5 |
| Proline | 2 |
| Glycine | 7 |
| Alanine | 2 |
| Cysteine | 6 |
| Valine | 4 |
| Isoleucine | 2 |
| Leucine | 3 |
| Tyrosine | 3 |
| Phenylalanine | 3 |
| Histidine | 3 |
| Lysine | 1 |
| Arginine | 7 | and a molecular weight of 6600 ± 10 %.

15. A polypeptide as claimed in claim 1, having the following composition of amino-acids:

| Amino acids | Number of molecules |
| --- | --- |
| Aspartic acid | 6 |
| Threonine | 1 |
| Serine | 4 |
| Glutamic acid | 4 |
| Proline | 2 |
| Glycine | 6 |
| Alanine | 2 |
| Cysteine | 6 |
| Valine | 4 |
| Isoleucine | 1 |
| Leucine | 2 |
| Tyrosine | 3 |
| Phenylalanine | 3 |
| Histidine | 3 |
| Lysine | 1 |
| Arginine | 6 |

16. A process for isolating polypeptides from sea-anemones which comprises extracting sea-anemones with water or a homogeneous mixture of water and a water-miscible organic solvent, contacting the extract as a weakly acid pH with an ion exchanger having acid functional groups, separating the liquid from the ion exchanger, and subsequently contacting the ion exchanger with a weakly basic aqueous medium to desorb the polypeptides therefrom.

17. A process for isolating polypeptides from sea-anemones which comprises extracting sea-anemones with water or a homogeneous mixture of water and a water-miscible organic solvent, contacting the extract with a water-insoluble trypsin resin, separating the trypsin resin from the extract, and subsequently contacting the trypsin resin with an aqueous acid medium at a pH of 1 to 3 to desorb the polypeptides therefrom.

* * * * *

UNITED STATES PATENT AND TRADEMARK OFFICE
CERTIFICATE OF CORRECTION

PATENT NO. : 3,951,939
DATED : April 20, 1976
INVENTOR(S) : Hans Fritz et al

It is certified that error appears in the above—identified patent and that said Letters Patent are hereby corrected as shown below:

In the Heading: Item [30], under "Foreign Application Priority Data" and before "July 7, 1973," insert --January 8, 1972 Germany 22 00 828--.

Signed and Sealed this

Sixth Day of July 1976

[SEAL]

Attest:

RUTH C. MASON
*Attesting Officer*

C. MARSHALL DANN
*Commissioner of Patents and Trademarks*